__United States Patent__ [19]

Diana et al.

[11] 4,096,280

[45] Jun. 20, 1978

[54] ARYLENEDIOXY-BIS-DIKETONES

[75] Inventors: Guy Dominic Diana, Stephentown; Philip Michael Carabateas, Schodack, both of N.Y.

[73] Assignee: Sterling Drug Inc., New York, N.Y.

[21] Appl. No.: 761,944

[22] Filed: Jan. 24, 1977

[51] Int. Cl.$^2$ .................. C07C 49/84; A01N 9/24
[52] U.S. Cl. ................... 424/331; 260/590 R
[58] Field of Search ................ 260/590 R; 424/331

[56] References Cited

U.S. PATENT DOCUMENTS

| | | | |
|---|---|---|---|
| 3,541,155 | 11/1970 | D'Amico | 260/590 R |
| 3,721,704 | 3/1973 | Dexter | 260/590 R |
| 3,917,718 | 11/1975 | Collins | 260/590 R |
| 3,933,837 | 1/1976 | Collins | 424/282 |

Primary Examiner—James O. Thomas, Jr.
Assistant Examiner—James H. Reamer
Attorney, Agent, or Firm—Thomas L. Johnson; B. Woodrow Wyatt

[57] ABSTRACT

Phenylenedioxy-bis-dikeones having the formula

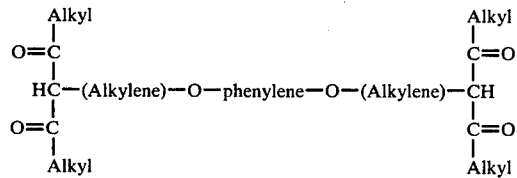

useful as antiviral agents, are prepared by etherification of dihydric phenols and alkylation of beta-diketones.

16 Claims, No Drawings

ARYLENEDIOXY-BIS-DIKETONES

BACKGROUND OF THE INVENTION (a) Field of the Invention

This invention relates to novel arylenedioxy-bis-diketones, to the preparation thereof, and to compositions and methods of use thereof as antiviral agents.

(b) Description of the Prior Art

Toray Industries British Pat. No. 1,200,834 (Aug. 5, 1970) discloses acyclic substances useful as intermediates for preparing surface active agents, lubricants and cosmetic perfumes. Among the substances disclosed are aliphatic diketones such as $(CH_3CO)_2CHC(CH_3)=CHCH_2CH_2C(CH_3)=CHCH(COCH_3)_2$.

Collins and Diana U.S. Pat. No. 3,933,837 (Jan. 20, 1976) discloses aryloxyalkyldiketones having antiviral activity, including compounds of the structure

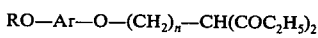

RO—Ar—O—$(CH_2)_n$—CH(COC$_2$H$_5$)$_2$ wherein Ar is phenylene or substituted phenylene, and R is hydrogen, alkyl or benzyl.

SUMMARY OF THE INVENTION

In a composition of matter aspect, the invention relates to compounds of the formula

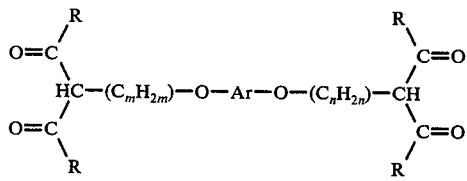

wherein:
R is alkyl of 1-4 carbon atoms;
Ar is 1,3- or 1,4-phenylene in which the phenyl ring can be further substituted by one or two methyl, ethyl or halo groups;
m and n are integers from 3 to 7, the sum of m and n ranging from 7 to 14.

In a further composition of matter aspect, the invention relates to a composition for combatting viruses which comprises an antivirally effective amount of at least one compound of formula I in admixture with a suitable carrier or diluent.

In a process aspect, the invention relates to a process for preparing a compound of formula I which comprises:

(a) interacting a compound of the formula HO—Ar—OH successively with molar equivalent amounts of compounds of the formulas Hal—$(C_mH_{2m})$—CH(COR)$_2$ and Hal—$(C_nH_{2n})$—CH(COR)$_2$, where Hal is bromine or iodine, or, where m an n are identical integers, with at least two molar equivalents of Hal—$(C_mH_{2m})$—CH(COR)$_2$, all in the presence of a base in an inert organic solvent; or (b) interacting a compound of the formula Hal—$(C_mH_{2m})$—O—Ar—O—$(C_nH_{2n})$—Hal, where Hal is bromine or iodine, with an alkali metal salt or heavy metal chelate of a diketone, RCOCH$_2$COR, in an inert organic solvent.

In a further process aspect, the invention relates to a method of combatting viruses which comprises contacting the locus of said viruses with a composition containing an anti-virally effective amount of at least one compound of formula I in admixture with a suitable carrier or diluent.

DETAILED DESCRIPTION INCLUSIVE OF PREFERRED EMBODIMENTS

The compounds of formula I are prepared by either of two processes which however are closely related chemically since they both involve elimination of hydrogen halide in the presence of a base.

The first synthetic approach comprises the reaction of a difunctional phenol, HO—Ar—OH, with a haloalkyldiketone in the presence of a base. The base is preferably one which converts the phenol to its alkali metal salt and includes such bases as sodium hydroxide, lithium hydride, potassium hydroxide, potassium carbonate and the like. The reaction takes place in an inert organic solvent, slowly at ambient temperature (20° C.) and more rapidly at elevated temperatures, preferably between about 50° C. and 100° C. In the haloalkyldiketone the halogen atom is preferably bromine or iodine.

In the case where m is different from n in formula I, the reaction is carried out stepwise, first with one molar equivalent, relative to the bisphenol, of Hal—$(C_mH_{2m})$—CH(COR)$_2$ to produce a hydroxyaryloxyalkyldiketone of the formula (ROC)$_2$CH—$(C_mH_{2m})$—O—Ar—OH; and second with one molar equivalent or an excess of Hal—$(C_nH_{2n})$—CH(COR)$_2$.

In the case where m is the same as n in formula I, the reaction can be carried out in a single step, with two or more molar equivalents of Hal—$(C_mH_{2m})$—CH(COR)$_2$.

The intermediate haloalkyldiketones are prepared by interacting an alkali metal enolate salt or heavy metal chelate of a diketone (RCO)$_2$CH$_2$ with an alkylene dihalide, Hal—$(C_mH_{2m})$—Hal or Hal—$(C_nH_{2n})$—Hal. The reaction takes place in an inert solvent under anhydrous conditions at ambient temperature or slightly above (20°-70° C.) using equimolar quantities of reactants or a stoichiometric excess of dihalide.

The second synthetic approach comprises the reaction of a phenylene-bis(oxyalkyl halide), Hal—$(C_mH_{2m})$—O—Ar—O—$(C_nH_{2n})$—Hal, wherein Hal is preferably bromine or iodine, with an alkali metal salt or heavy metal chelate of a diketone, RCOCH$_2$COR, in an inert organic solvent. The reaction is analogous to that used for the preparation of the intermediate haloalkyldiketones in the first synthetic approach.

The intermediates, Hal—$(C_mH_{2m})$—O—Ar—O—$(C_nH_{2n})$—Hal, are prepared by a method analogous to the final step of the first synthetic approach, that is by stepwise reaction of a bisphenol with equimolar quantities of Hal—$(C_mH_{2m})$—Hal and Hal—$(C_nH_{2n})$—Hal; or with an excess of Hal—$(C_mH_{2m})$—Hal, if m is identical with n.

The compounds of formula I where m is identical with n are preferred because of the relative simplicity of their preparation. Compounds where $C_mH_{2m}$ and $C_nH_{2n}$ are straight chain alkylene are also ordinarily preferred, although branched chain compounds are clearly within the purview of the invention.

In compounds of formula I where the Ar nucleus is substituted by halo, the halo group(s) can be any of the four halogens, fluorine, chlorine, bromine or iodine.

The structures of the compounds of the invention were established by the modes of synthesis, by elementary analysis, and by infrared and nuclear magnetic resonance spectral determinations.

Biological evaluation of the compounds of the invention has shown that they possess antiviral activity in vitro and in vivo. The in vitro testing of the compounds against Herpes virus type 2 showed that they had minimal growth inhibitory concentrations (mic) ranging from about 1.5 to about 25 micrograms per milliliter. The mic values were determined by standard serial dilution procedures.

The antiviral compositions are formulated by preparing a dilute solution or suspension in an organic or aqueous-organic medium, for example ethyl alcohol, acetone, dimethyl sulfoxide, and the like; and are applied to the locus to be disinfected by conventional means such as spraying, swabbing or immersing. Alternatively, the compounds can be formulated as ointments or creams by incorporating them in conventional ointment or cream bases, such as alkylpolyether alcohols, cetyl alcohol, stearyl alcohol and the like; as jellies by incorporating them in conventional jelly bases such as glycerin and tragacanth; or as aerosol sprays or foams.

The following examples will further illustrate the invention.

EXAMPLE 1

(a) 4-(6-Bromohexyl)-3,5-heptanedione.

A solution of 64.1 g of 3,5-heptanedione in 200 ml. of dimethylformamide was added over a period of 1 hour to a suspension of 3.65 g. of lithium hydride in 400 ml. of dimethylformamide. The mixture was stirred for one hour and 488 g. of 1,6-dibromohexane was then added all at once. The reaction mixture was warmed at 60°–70° C. for 24 hours. The volatile solvent was removed and the residue partitioned between water and methylene dichloride. The methylene dichloride solution was concentrated and the residue distilled to give 65.0 g. of 4-(6-bromohexyl)-3,5-heptanedione, b.p. 118°–124° C. (0.005 mm.).

By replacing the 1,6-dibromohexane in the foregoing preparation by a molar equivalent amount of 2-ethyl-1,3-dibromopropane or 2,4-dimethyl-1,5-dibromopentane, it is contemplated that there can be obtained, respectively, 4-(3-bromo-2-ethylpropyl)-3,5-heptanedione or 4-(5-bromo-2,4-dimethylpentyl)-3,5-heptanedione.

By replacing the 3,5-heptanedione in the foregoing preparation by a molar equivalent amount of 2,4-pentanedione, 5,7-undecanedione or 2,2,6,6-tetramethyl-3,5-heptanedione, it is contemplated that there can be obtained, respectively, 3-(6-bromohexyl)-2,4-pentanedione, 6-(6-bromohexyl)-5,7-undecanedione, or 4-(6-bromohexyl)-2,2,6,6-tetramethyl-3,5-heptanedione.

(b) 1,3-Bis(7,7-dipropionylheptyloxy)benzene

[I; R is $CH_3CH_2$, Ar is 1,3-phenylene, $C_mH_{2m}=C_nH_{2n}=(CH_2)_6$]. Systematic nomenclature: 4,4'-[(1,3-Phenylenedioxy)bis(1,6-hexanediyl)]bis[3,5-heptanedione].

A mixture of 5.5 g. (0.05 m.) of resorcinol, 29.1 g. (0.1 m.) of 4-(6-bromohexyl)-3,5-heptanedione, 28 g. of powdered anhydrous potassium carbonate and 3 g. of potassium iodide in 200 ml. of 2-butanone was heated at reflux for 24 hours. The reaction mixture was filtered and the filtrate concentrated in vacuo. The residue was dissolved in methylene dichloride and the solution filtered and concentrated in vacuo. The residual material was distilled in vacuo (0.01 mm.) to remove material boiling up to 150° C. The remaining material was dissolved in ether, treated with activated charcoal, filtered and concentrated in vacuo. The residue was chromatographed on a column of 300 g. of silica and eluted with an equal volume mixture of ether and hexane, collecting 150 ml. fractions. The first two fractions were combined and concentrated to give 13.8 g. of 1,3-bis(7,7-dipropionylheptyloxy)benzene as a viscous yellow oil. p Anal. Calcd. for $C_{32}H_{50}O_6$: C, 72.42; H, 9.50. Found: C, 72.22; H, 9.56.

1,3-Bis(7,7-dipropionylheptyloxy)benzene was found to have a minimum inhibitory concentration in vitro of 12 micrograms per milliliter against Herpes virus 2.

By replacing the 4-(6-bromohexyl)-3,5-heptanedione in the foregoing preparation by a molar equivalent amount of 4-(3-bromo-2-ethylpropyl)-3,5-heptanedione, 4-(5-bromo-2,4-dimethylpentyl)-3,5-heptanedione, 3-(6-bromohexyl)-2,4-pentanedione, 6-(6-bromohexyl)-5,7-undecanedione or 4-(6-bromohexyl)-2,2,6,6-tetramethyl-3,5-heptanedione, it is contemplated that there can be obtained, respectively, 1,3-bis(4,4-dipropionyl-2-ethylbutyloxy)benzene [I; R is $CH_3CH_2$, Ar is 1,3-phenylene, $C_mH_{2m}=C_nH_{2n}=CH_2CH(C_2H_5)CH_2$]; 1,3-bis(6,6-dipropionyl-2,4-dimethylhexyloxy)benzene [I; R is $CH_3CH_2$, Ar is 1,3-phenylene, $C_mH_{2m}=C_nH_{2n}=CH_2CH(CH_3)CH_2CH(CH_3)CH_2$], 1,3-bis(7,7-diacetylheptyloxy)benzene [I; R is $CH_3$, Ar is 1,3-phenylene, $C_mH_{2m}=C_nH_{2n}=(CH_2)_6$]; or 1,3-bis[7,7-bis(trimethylacetyl)heptyloxy]benzene [I; R is $(CH_3)_3C$, Ar is 1,3-phenylene, $C_mH_{2m}=C_nH_{2n}=(CH_2)_6$].

EXAMPLE 2

1,4-Bis(7,7-dipropionylheptyloxy)benzene

[I; R is $CH_3CH_2$, Ar is 1,4-phenylene, $C_mH_{2m}=C_nH_{2n}=(CH_2)_6$]. Systematic nomenclature: 4,4'-[(1,4-Phenylenedioxy)bis(1,6-hexanediyl)]bis[3,5-heptanedione].

Prepared from 2.74 g. of hydroquinone and 17.5 g. of 4-(6-bromohexyl)-3,5-heptanedione according to the procedure of Example 1, part (b). The product was distilled at 235°–245° C. (0.03 mm.) and chromatographed on silica. The crystalline fractions were recrystallized from ether to give 2.2 g. of 1,4-bis(7,7-dipropionylheptyloxy)benzene, m.p. 56°–57° C.

Anal. Calcd. for $C_{32}H_{50}O_6$: C, 72.42; H, 9.50. Found: C, 72.19; H, 9.70.

1,4-Bis(7,7-dipropionylheptyloxy)benzene was found to have a maximum inhibitory concentration in vitro of 6 micrograms per milliliter against Herpes virus 2. It was also effective in controlling Herpes virus 2 infections in the rabbit eye.

EXAMPLE 3

1,4-Bis(8,8-dipropionyloctyloxy)benzene

[I; R is $CH_2CH_2$, Ar is 1,4-phenylene, $C_mH_{2m}=C_nH_{2n}=(CH_2)_7$]. Systematic nomenclature: 4,4'-[(1,4-Phenylenedioxy)bis(1,7-heptanediyl)]bis[3,5-heptanedione].

Prepared from 3.8 g. of hydroquinone and 21 g. of 4-(7-bromoheptyl)-3,5-heptanedione (b.p. 125°–127° C., 0.03 mm.) according to the procedure of Example 1, part (b). The product was obtained in crystalline form and recrystallized from methanol to give 4.0 g. of 1,4-bis(8,8-dipropionyloctyloxy)benzene, m.p. 56°–57° C.

Anal. Calcd. for $C_{34}H_{54}O_6$: C, 73.09; H, 9.74. Found: C, 73.51; H, 9.86. 1,4-Bis(8,8-dipropionyloctyloxy)benzene was found to have a minimum inhibitory concentration in vitro of 25 micrograms per milliliter against Herpes virus 2.

EXAMPLE 4

1,4-Bis(7,7-dipropionylheptyloxy)-2,5-dichlorobenzene

[I; R is $CH_3CH_2$, Ar is 2,5-dichloro-1,4-phenylene, $C_mH_{2m}=C_nH_{2n}=(CH_2)_6$]. Systematic nomenclature: 4,4'-[2,5-Dichloro-1,4-phenylenedioxy]-bis(1,6-hexanediyl)bis[3,5-heptanedione].

Prepared from 9.0 g. of 2,5-dichlorohydroquinone and 35.0 g. of 4-(6-bromohexyl)-3,5-heptanedione according to the procedure of Example 1, part (b). The product was distilled at 300° C. (0.005 mm.), chromatographed on 1.2 kg. of silica gel, and eluted with a mixture of 4 parts of hexane and 1 part of ethyl acetate. There was thus obtained 13.1 g of 1,4-bis(7,7-dipropionylheptyloxy)-2,5-dichlorobenzene as a yellow oil.

Anal. Calcd. for $C_{32}H_{48}Cl_2O_6$: C, 64.10; H, 8.07; Cl, 11.82. Found: C, 64,38; H, 8.03; Cl, 11.78.

1,4-Bis(7,7-dipropionylheptyloxy)-2,5-dichlorobenzene was found to have a minimum inhibitory concentration in vitro of 6 micrograms per milliliter against Herpes virus 2.

EXAMPLE 5

1,4-Bis(6,6-dipropionylhexyloxy)benzene

[I; R is $CH_3CH_2$, Ar is 1,4-phenylene, $C_mH_{2m}=C_nH_{2n}=(CH_2)_5$]. Systematic nomenclature: 4,4'-[(1,4-Phenylenedioxy)bis(5,1-pentanediyl)]bis[3,5-heptanedione].

Prepared from 3.93 g. of hydroquinone and 19.8 g. of 4-(5-bromopentyl)-3,5-heptanedione (b.p. 115°–117° C., 0.05 mm.) according to the procedure of Example 1, part (b). The product (1.2 g.) was obtained as a colorless waxy solid.

Anal. Calcd. for $C_{30}H_{46}O_6$: C, 71.68; H, 9.22. Found: C, 71.63; H, 9.58.

1,4-Bis(6,6-dipropionylhexyloxy)benzene was found to have a minimum inhibitory concentration in vitro of 3 micrograms per milliliter against Herpes virus 2.

EXAMPLE 6

1,4-Bis(7,7-dipropionylheptyloxy)-2-methylbenzene

[I; R is $CH_3CH_2$, Ar is 2-methyl-1,4-phenylene, $C_mH_{2m}=C_nH_{2n}=(CH_2)_6$]. Systematic nomenclature: 4,4'-[2-Methyl-1,4-phenylenedioxy]bis(1,6-hexanediyl)-bis[3,5-heptanedione].

Prepared from 6.2 g. of 2-methylhydroquinone and 43.5 g. 4-(6-bromohexyl)-3,5-heptanedione according to the procedure of Example 1, part (b). The product was distilled at 250°–255° C. (0.0005 mm.) to give 11.8 g. of 1,4-bis(7,7-dipropionylheptyloxy)-2-methylbenzene as a pale yellow oil.

Anal. Calcd. for $C_{33}H_{52}O_6$: C, 72.76; H, 9.62. Found: C, 72.87; H, 9.74.

1,4-Bis(7,7-dipropionylheptyloxy)-2-methylbenzene was found to have a minimum inhibitory concentration in vitro of 25 micrograms per millimeter against Herpes virus 2.

EXAMPLE 7

1,4-Bis(7,7-dipropionylheptyloxy)-2-chlorobenzene

[I; R is $CH_3CH_2$, Ar is 2-chloro-1,4-phenylene, $C_mH_{2m}=C_nH_{2n}=(CH_2)_6$]. Systematic nomenclature: 4,4'-[2-Chloro-1,4-phenylenedioxy]bis(1,6-hexanediyl(-bis[3,5-heptanedione].

Prepared from 7.2 g. of 2-chlorohydroquinone and 43.5 g. of 4-(6-bromohexyl)-3,5-heptanedione according to the procedure of Example 1, part (b). The product was distilled at 260°–265° C. (0.01 mm.) to give 15.1 g. of 1,4-bis(7,7-dipropionylheptyloxy)-2-chlorobenzene as an orange oil.

Anal. Calcd. for $C_{32}H_{49}ClO_6$: C, 68.00; H, 8.74; Cl, 6.27. Found: C, 68.33; H, 9.04; Cl, 6.44.

1,4-Bis(7,7-dipropionylheptyloxy)-2-chlorobenzene was found to have a minimum inhibitory concentration in vitro of 6 micrograms per milliliter against Herpes virus 2.

By using procedures analogous to that of Example 1(b) and 7 and substituting for the 2-chlorohydroquinone of Example 7 2-fluorohydroquinone, 2-bromohydroquinone, 2-iodohydroquinone or 2-ethylhydroquinone, it is contemplated that there can be obtained, respectively, 1,4-bis(7,7-dipropionylheptyloxy)-2-fluorobenzene, 1,4-bis(7,7-dipropionylheptyloxy)-2-bromobenzene, 1,4-bis(7,7-dipropionylheptyloxy)-2-iodobenzene, or 1,4-bis(7,7-dipropionylheptyloxy)-2-ethylbenzene.

EXAMPLE 8

(a) 1,4-Bis(4-bromobutyloxy)benzene.

A solution of 14.2 g. (0.129 m.) of hydroquinone in 50 ml. of ethanol was added to a solution of 11.6 g. (0.281 m.) of sodium hydroxide in 250 ml. of ethanol, and the mixture was stirred for 15 minutes at room temperature and at 40°–45° C. for 30 minutes. The mixture was then cooled to 4° C. and 168 g. (0.780 m.) of 1,4-dibromobutane was added. The reaction mixture was stirred at room temperature for 6 hours and heated at reflux overnight. The mixture was partitioned between ether and water, the water layer washed with methylene dichloride and the combined organic layers dried over anhydrous sodium sulfate and concentrated. The residue was distilled (75°–85° C., 15 mm.) to remove excess, 1,4-dibromobutane, and the residue crystallized from methanol and recrystallized from isopropyl acetate to give 21.6 g. of 1,4-bis(4-bromobutyloxy)benzene, m.p. 89°–91° C.

(b) 1,4-Bis(5,5-dipropionylpentyloxy)benzene

[I; R is $CH_3CH_2$ Ar is 1,4-phenylene, $C_mH_{2m}=C_nH_{2n}=(CH_2)_4$]. Systematic nomenclature: 4,4'-[(1,4-Phenylenedioxy)bis(4,1-butanediyl)]bis[3,5-heptanedione].

To a suspension of 1.79 g. of lithium hydride in 185 ml. of dimethylformamide was added, dropwise, 31.8 g. of 3,5-heptanedione over a 20 minute period. To the resulting lithium salt of 3,5-heptanedione was added a solution of 21.5 g. of 1,4-bis(4-bromobutyloxy)benzene in 100 ml. of dimethylformamide, and the mixture was stirred at 60°–70° C. for two days. The organic fraction of the product was isolated and unreacted 3,5-heptanedione removed by distillation (65°–68° C., 15 mm.). The remaining product crystallized and was recrystallized from an isopropyl alcohol-hexane mixture to give 6.5 g. of 1,4-bis(5,5-dipropionylpentyloxy)benzene, m.p. 51°–52° C.

Anal. Calcd. for $C_{28}H_{42}O_6$: C, 70.86; H, 8.92. Found: C, 70.58; H, 8.88.

1,4-Bis(5,5-dipropionylpentyloxy)benzene was found to have a minimum inhibitory concentration in vitro of 1.5 micrograms per milliliter against Herpes virus 2.

EXAMPLE 9

(a) 4-(3-Bromopropyloxy)phenol.

A mixture of 88.0 g. (0.80 m.) of hydroquinone, 161.6 g. (0.80 m.) of 1,3-dibromopropane and 55.2 g. (0.40 m.) of potassium carbonate in 2 liters of 2-butanone was heated at reflux for 24 hours. The reaction mixture was filtered and the filtrate concentrated in vacuo. The solid and liquid phases of the residue were separated, and the liquid fraction was chromatographed on silica gel using chloroform-acetonitrile (95:5) as the eluant. There was thus obtained 37.2 g. of 4-(3-bromopropyloxy)phenol as a light brown oil which was used directly in the next reaction.

(b) 1-(4-Bromobutyloxy)-4-(3-bromopropyloxy)benzene.

A mixture of 39.7 g. (0.172 m.) of 4-(3-bromopropyloxy)phenol, 148.2 g. (0.686 m.) of 1,4-dibromobutane and 10.8 g. of potassium carbonate in 1000 ml. of 2-butanone was heated at reflux for two days. The reaction mixture was filtered and concentrated in vacuo and the residue distilled to remove volatile starting materials. The residue was recrystallized from acetonitrile and then from ethanol to give 21.7 g. of 1-(4-bromobutyloxy)-4-(3-bromopropyloxy)benzene, m.p. 73°–76° C.

(c) 1-(4-Iodobutyloxy)-4-(3-iodopropyloxy)benzene.

A mixture of 31 g. (0.085 m.) of 1-(4-bromobutyloxy)-4-(3-bromopropyloxy)benzene and 25.5 g. (0.17 m.) of sodium iodide in 1000 ml. of acetone was heated at reflux for 90 minutes. The reaction mixture was filtered and the filtrate evaporated to remove the acetone. The residue was partitioned between water and methylene dichloride, and the latter dried over anhydrous magnesium sulfate and concentrated in vacuo. The residue was dried in vacuo (0.5 mm.) for 45 minutes to give 38.0 g. of 1-(4-iodobutyloxy)-4-(3-iodopropyloxy)benzene as a waxy solid used directly in the next reaction.

(d) 1-(5,5-Dipropionylpentyloxy)-4-(4,4-dipropionylbutyloxy)benzene

[I; R is $CH_3CH_2$; Ar is 1,4-phenylene, $C_mH_{2m}=(CH_2)_4$, $C_nH_{2n}=(CH_2)_3$] was prepared from 38.0 g. of 1-(4-iodobutyloxy)-4-(3-iodopropyloxy)benzene and the lithium salt derived from 21.7 g. of 3,5-heptanedione according to the procedure of Example 8, part (b). The crude product was chromatographed on activated magnesium silicate, and eluted with the solvent series hexane-benzene-ether. An equal volume mixture of ether and benzene brought out the pure compound, 4.1 g. of 1-(5,5-dipropionylpentyloxy)-4-(4,4-dipropionylbutyloxy)benzene as a light yellow oil, structure confirmed by infrared and nuclear magnetic resonance spectra.

Anal. Calcd. for $C_{27}H_{40}O_6$: C, 70.40; H, 8.75. Found: C, 70.69; H, 8.63.

We claim:

1. A compound of the formula

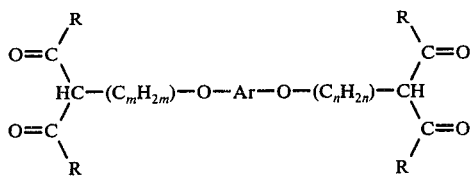

wherein:
R is alkyl of 1–4 carbon atoms;
Ar is 1,3- or 1,4-phenylene in which the phenyl ring can be further substituted by one or two methyl, ethyl or halo groups;
$m$ and $n$ are integers from 3 to 7, the sum of $m$ and $n$ ranging from 7 to 14.

2. A compound according to claim 1 wherein Ar is 1,4-phenylene and $m$ and $n$ are identical integers.

3. A compound according to claim 1 wherein Ar is 1,4-phenylene, $m$ and $n$ are identical integers and R is ethyl.

4. 1,4-Bis(7,7-dipropionylheptyloxy)benzene, according to claim 3.

5. 1,3-Bis(7,7-dipropionylheptyloxy)benzene, according to claim 1.

6. 1,4-Bis(8,8-dipropionyloctyloxy)benzene, according to claim 3.

7. 1,4-Bis(7,7-dipropionylheptyloxy)-2,5-dichlorobenzene, according to claim 1.

8. 1,4-Bis(6,6-dipropionylhexyloxy)benzene, according to claim 3.

9. 1,4-Bis(7,7-dipropionylheptyloxy)-2-methylbenzene, according to claim 1.

10. 1,4-Bis(7,7-dipropionylheptyloxy)-2-chlorobenzene, according to claim 1.

11. 1,4-Bis(5,5-dipropionylpentyloxy)benzene, according to claim 3.

12. 1-(5,5-Dipropionylpentyloxy)-4-(4,4-dipropionylbutyloxy)benzene, according to claim 1.

13. A composition for combatting viruses which comprises an antivirally effective amount of at least one compound according to claim 1 in admixture with a suitable carrier or diluent.

14. A composition according to claim 13 wherein the antivirally effective compound is 1,4-bis(5,5-dipropionylpentyloxy)benzene.

15. A method for combatting viruses which comprises contacting the locus of said viruses with a composition containing an antivirally effective amount of at least one compound according to claim 1 in admixture with a suitable carrier or diluent.

16. A method according to claim 15 wherein the anti-virally effective compound is 1,4-bis(5,5-dipropionylpentyloxy)benzene.

* * * * *